United States Patent [19]

Van Dyke, Jr. et al.

[11] 4,361,566
[45] Nov. 30, 1982

[54] TETRAHYDRO β-CARBOLINES HAVING ANTIHYPERTENSIVE ACTIVITY

[75] Inventors: John W. Van Dyke, Jr.; Elva Kurchacova, both of Elkhart, Ind.

[73] Assignee: Miles Laboratories, Inc., Elkhart, Ind.

[21] Appl. No.: 255,544

[22] Filed: Apr. 20, 1981

Related U.S. Application Data

[62] Division of Ser. No. 176,407, Aug. 8, 1980, Pat. No. 4,291,039.

[51] Int. Cl.³ ................... C07D 487/14; A61K 31/44
[52] U.S. Cl. ..................................... 424/256; 546/85; 546/86
[58] Field of Search .................... 546/85, 86; 424/256

[56] References Cited

U.S. PATENT DOCUMENTS 3,202,666  8/1964  Szuszkovica ................. 260/295
3,202,667  8/1965  Szuszkovica et al. ......... 260/295

FOREIGN PATENT DOCUMENTS 655046  9/1965  South Africa .

OTHER PUBLICATIONS

Harvey et al., Journal of the Chemical Society, London, pp. 153–159, 1941.
Saxena et al., Chemical Abstracts, vol. 79, No. 11, 61, 395-k, Sep. 17, 1973.

*Primary Examiner*—Alan L. Rotman
*Attorney, Agent, or Firm*—Jerome L. Jeffers

[57] ABSTRACT

Disclosed are novel tetrahydro β-carbolines of the formula:

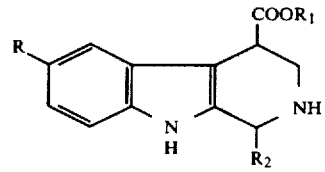

wherein R is H, $OCH_3$ or F; $R_1$ is H or $CH_3$ and $R_2$ is H or $COOR_3$ where $R_3$ is H or $CH_3$. These compounds are useful as antihypertensive agents.

14 Claims, No Drawings

TETRAHYDRO β-CARBOLINES HAVING ANTIHYPERTENSIVE ACTIVITY

This is a division of application Ser. No. 176,407, filed Aug. 8, 1980 now U.S. Pat. No. 4,291,039 issued Oct. 22, 1981.

BACKGROUND OF THE INVENTION

U.S. Pat. No. 3,202,666, issued Aug. 24, 1965, discloses substituted 9H-pyrido (3,4-b) indole-1-carboxylic acid and derivatives thereof characterized by the formula:

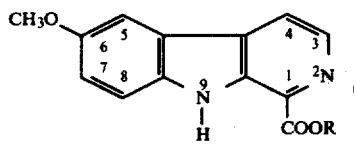

where R is hydrogen or a lower alkyl group of 1–4 carbon atoms. These compounds are said to have significant sedative and antiparasitic acitivity.

In U.S. Pat. No. 3,202,667, issued Aug. 24, 1965 compounds of the formula:

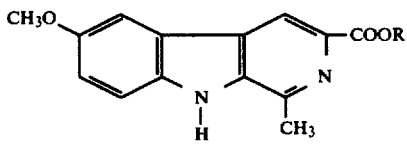

where R is hydrogen or lower alkyl of 1–4 carbon atoms are disclosed as having utility as anti-inflammatory and sedative agents.

South African Patent No. 65/5046 dated Sept. 16, 1965, discloses β-carboline derivatives of the formula:

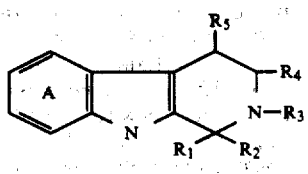

where $R_1$ can be hydrogen, $R_2$ can be carboxy or alkoxycarbonyl, $R_3$ can be hydrogen and $R_4$ and $R_5$ are hydrogen or alkyl radicals. The compounds disclosed in this patent are further defined in that the benzene ring A may be substituted by one or more alkoxy radicals. These compounds are disclosed as having utility as analgesic agents.

SUMMARY OF THE INVENTION

The present invention involves novel tetrahydro β-carbolines of the formula:

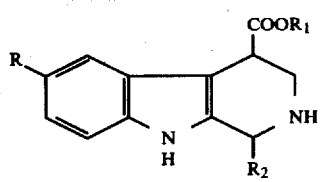

In the above formula R is H, $OCH_3$ or F; $R_1$ is H or $CH_3$ and $R_2$ is H, COOH or $COOCH_3$. The description of these compounds is further limited in that R is F or $OCH_3$ only when $R_2$ is H.

These compounds have therapeutic utility as antihypertensive agents.

DESCRIPTION OF THE INVENTION

The compounds of this invention are prepared according to Scheme I where R is defined and limited above.

Referring to Scheme I, the indole β-aminoacid 1 is treated at room temperature with an equivalent amount of glyoxalic acid dissolved in $H_2O$ (e.g., 35 mmole dissolved in 100 ml of $H_2O$). The pH of the solution is adjusted to pH 4 by adding base (e.g., 10% KOH, 10% $K_2CO_3$, etc.). The diacid or monoacid monoester 2 is filtered after stirring at room temperature for 24 hours.

Compound 2 is converted to the diester 4 by treating a methanol solution with an equivalent amount of thionyl chloride at 0° C. After addition, the mixture is stirred at room temperature overnight. The free base of the diester is liberated from the hydrochloride salt using a base (e.g., 6% $K_2CO_3$). One equivalent of HCl (4 N HCl in dioxane was used; other solvents are also suitable) is added and the diester hydrochloride is filtered.

Compound 2 is converted to compound 3 by refluxing in ≈10% HCl for 2 hours.

Compound 5 is prepared in a manner similar to the preparation of compound 3.

SCHEME I

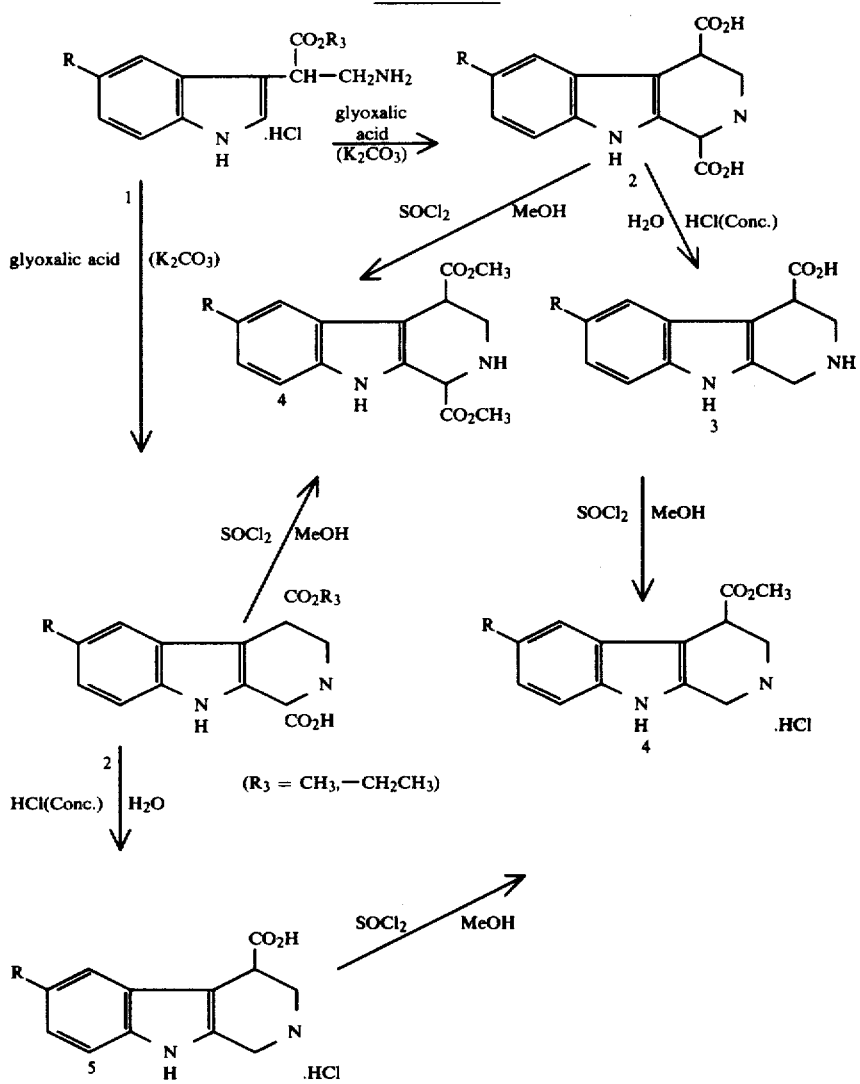

The preparation and pharmacological evaluation of these compounds is further illustrated by the following examples:

EXAMPLE 1

1,2,3,4-Tetrahydro-β-Carboline-1,4-Dicarboxylic Acid (TR-8021)

3-Amino-2-(3-indolyl)propanoic acid (6 g; 0.03 mole) was mixed with 55 ml of water. Then glyoxalic acid (80% in water) (3 g; 30 mmole) dissolved in 50 ml of water was added and with rapid stirring 10% $K_2CO_3$ solution was added to pH 4.00. The mixture was stirred for a period of 3 days. A white precipitate was collected, washed with 400 ml of water and dried overnight with isopropyl alcohol. Yield 3 g (38%) mp 230°–231° C.

Anal. calcd. for $C_{13}H_{12}N_2O_4$: C, 60.05; H, 4.65; N, 10.76. Found: C, 60.02; H, 4.71; N, 10.76.

EXAMPLE 2

Dimethyl-1,2,3,4-Tetrahydro-β-Carboline-1-4-Dicarboxylate Hydrochloride (TR-8022)

1,2,3,4-Tetrahydro-β-carboline-1,4-dicarboxylic acid (2 g; 0.007 mole) prepared in Example 1 was dissolved in 50 ml of methanol. It was cooled in a dry-ice acetone bath at 0° C. Then thionyl chloride (1.38 ml, 0.019 mole) was added dropwise. The mixture was stirred at room temperature for 24 hours and the solvent removed in vacuo. The residue was partitioned in ethyl acetate and 6% $K_2CO_3$ solution. The organic layer was dried over $MgSO_4$, filtered, and treated with 4 N-HCl in dioxane to pH 5. A white precipitate was collected by filtration, washed with cooled ethyl acetate and dried in an oven at 60° C. for 24 hours. Yield 0.7 g (30%) mp 183°–184° C.

Anal. calcd. for $C_{15}H_{17}ClN_2O_4$: C, 55.47; H, 5.28; N, 8.63. Found: C, 55.11; H, 5.44; N, 8.42.

EXAMPLE 3

1,2,3,4-Tetrahydro-β-Carboline-4-Carboxylic Acid Hydrochloride (TR-8025)

Four (4) g; 0.16 mole of 1,2,3,4-tetrahydro-β-carboline-1,4-dicarboxylic acid (TR-8021) prepared in Example 1 was mixed with 40 ml concentrated HCl and 120 ml of water. The mixture was refluxed at 80° C. (oil-bath) for 2 hours. A white precipitate was collected by filtration, and washed with small amount of cooled water. The crude material was boiled in water, filtered through celite and cooled. The precipitate was collected and dried in the oven at 60° C. Yield: 3 g; (74%). MP 280°–281° C.

Anal. calcd. for $C_{12}H_{12}N_2O_2 \cdot HCl$: C, 57.03; H, 5.19; N, 11.09. Found: C, 56.77; H, 5.36; N, 10.96.

EXAMPLE 4

Methyl 1,2,3,4-Tetrahydro-β-Carboline-4-Carboxylate Hydrochloride (TR-8026)

1,2,3,4-Tetrahydro-β-carboline-4-carboxylic acid hydrochloride (3 g, 0.012 mole) (TR-8025) prepared in Example 3 was mixed with 50 ml of methanol. It was cooled at 0° C. Then thionylchloride (2 ml, 0.028 mole) was added dropwise. The mixture was stirred at room temperature for 24 hours. The solvent was removed in vacuo. The residue was partitioned in ethyl acetate/6% $K_2CO_3$ solution. The organic phase was dried over $MgSO_4$, filtered and treated with 4 NHCl in dioxane to pH=5. A white solid was collected. Yield: 2 g (62%) mp 246°–247° C.

Anal. calcd. for $C_{13}H_{14}N_2O_2 \cdot HCl$: C, 58.49; H, 5.67; N, 10.50. Found: C, 58.52; H, 5.95; N, 10.52.

EXAMPLE 5

Methyl 6-Methoxy-1,2,3,4-Tetrahydro-β-Carboline-4-Carboxylate Hydrochloride (TR-3938)

The procedures in Examples 1, 3 and 4 were followed starting with ethyl 3-amino-2-[3-(5-methoxyindolyl)]-propanoate hydrochloride. Yield, 28%. MP 253°–254° C.

Anal. calcd. for $C_{14}H_{17}ClN_2O_3$: C, 56.65; H, 5.77; N, 9.44. Found: C, 56.20; H, 5.72; N, 9.28.

EXAMPLE 6

6-Fluoro-1,2,3,4-Tetrahydro-β-Carboline-1,4-Dicarboxylic Acid (TR-8000)

TR-8000 was prepared as in Example 1 starting with 3-amino-2-(5-fluoro-3-indolyl)propanoic acid. Yield, 22%. MP 233°–234° C.

Anal. Calcd. for $C_{13}H_{11}FN_2O_4$: C, 56.16; H, 3.99; N, 10.08. Found: C, 55.20; H, 4.10; N, 9.92.

EXAMPLE 7

6-Fluoro-1,2,3,4-Tetrahydro-β-Carboline-4-Carboxylic Acid Hydrochloride (TR-8001)

TR-8001 was prepared as in Example 3 starting with TR-8000 (Example 6). Yield, 85%. MP 277°–278° C.

Anal. calcd. for $C_{12}H_{12}ClFN_2O_2$: C, 53.24; H, 4.47; N, 10.35. Found: C, 53.13; H, 4.41; N, 10.49.

EXAMPLE 8

Methyl 6-Fluoro-1,2,3,4-Tetrahydro-β-Carboline-4-Carboxylate Hydrochloride (TR-8003)

TR-8003 was prepared as in Example 4 starting with TR-8001 (Example 7). Yield, 70%. MP 257°–258° C.

Anal. calcd. for $C_{13}H_{14}ClFN_2O_2$: C, 54.84; H, 4.96; N, 9.84. Found: C, 54.85; H, 5.00; N, 9.90.

EXAMPLE 9

Methyl 6-Chloro-1,2,3,4-Tetrahydro-β-Carboline-4-Carboxylate Hydrochloride (TR-8161)

The procedures in Examples 1, 3 and 4 were followed starting with 3-amino-2-(5-chloro-3-indolyl)propanoic acid. Yield, 21%. MP 252°–254° C.

Anal. calcd. for $C_{13}H_{14}Cl_2N_2O_2$: C, 51.84; H, 4.68; N, 9.30. Found: C, 51.92; H, 4.71; N, 9.03.

EXAMPLE 10

Methyl 6-Methoxy-1,2,3,4-Tetrahydro-β-Carboline-1-Carboxylic Acid-4-Carboxylate (TR-8397)

Methyl 3-amino-2-(5-methoxyindol-3-yl) propionate (11 g; 0.083 mole) was mixed with 50 ml of water and glyoxylic (80% in water) (4.25 g; 0.038 mole) dissolved in 100 ml of water was added and a 10% $K_2CO_3$ solution was added with rapid stirring to pH 4.0. After four days of stirring the resultant white precipitate was collected, washed with 500 ml of water and dried overnight over isopropyl alcohol. Yield 10 g (80%). MP 223°–224° C.

Anal. calcd. for $C_{15}H_{16}N_2O_5$: C, 59.21; H, 5.30; N, 9.21. Found: C, 58.74; H, 5.46; N, 9.13.

EXAMPLE 11

Methyl 6-Fluoro-1,2,3,4-Tetrahydro-β-Carboline-1-Carboxylate Hydrochloride (TR-8229)

A. 6-fluoro-1,2,3,4-tetrahydro-β-carboline-1-carboxylic acid was prepared as follows:

Seven (7) g; 0.033 mole of 6-fluorotryptamine hydrochloride was mixed with 60 ml of water. At this point glyoxylic acid (80% in water) (3.5 g; 0.035 mole) dissolved in 50 ml of water was added and, with rapid stirring, 10% $K_2CO_3$ solution was added until the pH reached 4.0. The mixture was stirred for a period of 2 days resulting in a white precipitate which was collected, washed with 400 ml of water and dried overnight over 150 ml of propyl alcohol. Yield 4.5 g (58%) MP 237°–238° C.

Anal. calcd. for $C_{12}H_{11}N_2O_2$: C, 61.59; H, 4.74; N, 11.97. Found: C, 60.80; H, 4.67; N, 11.57.

B. The title compound was prepared by mixing 6-fluoro-1,2,3,4-tetrahydro-β-carboline-1-carboxylic acid (2 g; 0.0085 mole) with 60 ml of methanol. After cooling at 0° C., thionyl chloride (2 ml., 0.028 mole) was added dropwise and the mixture stirred at room temperature for 24 hours whereupon the solvent was removed in vacuo. The residue was partitioned in ethylacetate/6% $K_2CO_3$ solution whereupon the organic phase was dried over $MgSO_4$, filtered and treated with 4 N HCl in dioxane to pH 5. A white solid product was collected. Yield: 1.2 g (38%) MP 219°–220° C.

anal. calcd. for $C_{13}H_{18}FN_2O_2HCl$: C, 54.85; H, 5.00; N, 9.90. Found: C, 55.22; H, 4.97; N, 9.73.

DETERMINATION OF ANTI-HYPERTENSIVE ACTIVITY EXPERIMENTS IN RATS

The acute antihypertensive activity of test compounds was determined in rats made hypertensive by the procedure of A. Grollman, Proc. Soc. Exper. Biol. Med. 57:102 (1944) by applying a figure of eight (8) ligature to one (1) kidney and removing the contralateral kidney two weeks later. At least four weeks after the second operation, the rats were subjected to indirect systolic blood pressure measurements with an occluding cuff and pulse sensor applied to the tail. Measurements were made before and at 1, 2, 4, 6 and 8 hours after the oral administration of the test compounds at a dose of 10 mg/kg. Each compound was tested initially in five (5) rats and if it elicited a significant decrease in pressure at any of the observation periods, it was tested in another five (5) animals and results of the two (2) experiments were averaged. Statistical significance of differences between initial and post treatment values was determined by Wilcoxon's signed rank test (F. Wilcoxon and R. A. Wilcox, Some Rapid Approximate Statistical Procedures, Lederly Laboratories, Pearl River, 1964).

The results of these experiments are set out in Table I.

TABLE I

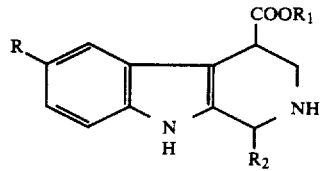

| Compound | R | $R_1$ | $R_2$ | $n^1$ | $C^2$ | 1 hr. | 2 hr. | 4 hr. | 6 hr. | 8 hr. | 2-8 hr. |
|---|---|---|---|---|---|---|---|---|---|---|---|
| TR-3938 | OCH3 | CH3 | H | 10 | 187 | 0 | −6 | −9* | +1 | +4 | −2 |
| TR-8000 | F | H | COOH | 5 | 193 | −4 | +1 | −1 | 0 | +4 | +1 |
| TR-8001 | F | H | H | 10 | 206 | −4 | −2 | −8* | −3 | 0 | −3 |
| TR-8003 | F | CH3 | H | 10 | 195 | −18* | −20* | −10 | −4 | +2 | −8 |
| TR-8021 | H | H | COOH | 10 | 192 | −14* | −18* | −16* | +8 | +17* | −3 |
| TR-8022 | H | CH3 | COOCH3 | 10 | 191 | −9* | −10 | −18* | −11* | −8 | −10 |
| TR-8025 | H | H | H | 5 | 188 | −10 | −6 | +5 | −4 | −3 | −2 |
| TR-8026 | H | CH3 | H | 5 | 176 | −8 | −7 | −2 | +5 | +1 | −1 |
| TR-8161 | Cl | CH3 | H | 5 | 182 | −3 | +8 | +5 | +7 | +5 | +6 |
| TR-8397 | OCH3 | CH3 | COOH | 5 | 188 | −1 | 1 | 1 | 3 | 12 | |
| TR-8229 | 7 | ** | COOCH3 | 5 | 184 | 4 | 1 | −4 | 1 | 7 | |

$^1$n = number of test animals
$^2$C = initial value
* = statistically significant
** = no substitution at 4-position The compounds of this invention possess unexpected pharmacological properties that render them useful as therapeutic agents for the treatment of hypertension in an individual for whom such therapy is indicated. The term individual is intended to mean a human being or an experimental animal that is used as a model for a human being. The effective dosage may vary from individual to individual but is easily determined by one skilled in the art without undue experimentation. Dose forms for the administration of the compounds of this invention may be prepared by recognized methods in the pharmaceutical sciences. Particular dose forms can be administered by conventional known methods of therapeutic administration such as oral, intravenous, parenteral or the like.

What is claimed is:

1. Tetrahydro β-carbolines of the formula:

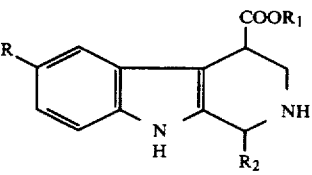

wherein R is $OCH_3$ or F; $R_1$ is H or $CH_3$ and $R_2$ is H.

2. A compound as described in claim 1 wherein R is $OCH_3$, $R_1$ is $CH_3$ and $R_2$ is H.

3. A compound as described in claim 1 wherein R is F, $R_1$ is H and $R_2$ is H.

4. A compound as described in claim 1 wherein R is F, $R_1$ is $CH_3$ and $R_2$ is H.

5. A compound as described in claim 1 wherein $R_1$ and $R_2$ are H.

6. A compound as described in claim 1 wherein $R_1$ is $CH_3$ and $R_2$ is H.

7. A compound as described in claim 1 in the form of its pharmaceutically acceptable, organic or inorganic acid addition salt.

8. A method of treating hypertension in an individual for whom such therapy is indicated which method comprises administering to such individual an antihypertensively effective amount of a compound characterized by the formula:

wherein R is $OCH_3$ or F; $R_1$ is H or $CH_3$ and $R_2$ is H.

9. The method of claim 8 wherein the compound administered is further defined in that R is $OCH_3$, $R_1$ is $CH_3$ and $R_2$ is H.

10. The method of claim 8 wherein the compound administered is further defined in that R is F, $R_1$ is H and $R_2$ is H.

11. The method of claim 8 wherein the compound administered is further defined in that R is F, $R_1$ is $CH_3$ and $R_2$ is H.

12. The method of claim 8 wherein the compound administered is further defined in that $R_1$ and $R_2$ are H.

13. The method of claim 8 wherein the compound administered is further defined in that $R_1$ is $CH_3$ and $R_2$ is H.

14. The method of claim 8 wherein the compound administered is in the form of its pharmaceutically acceptable, organic or inorganic acid addition salt.

* * * * *